United States Patent [19]

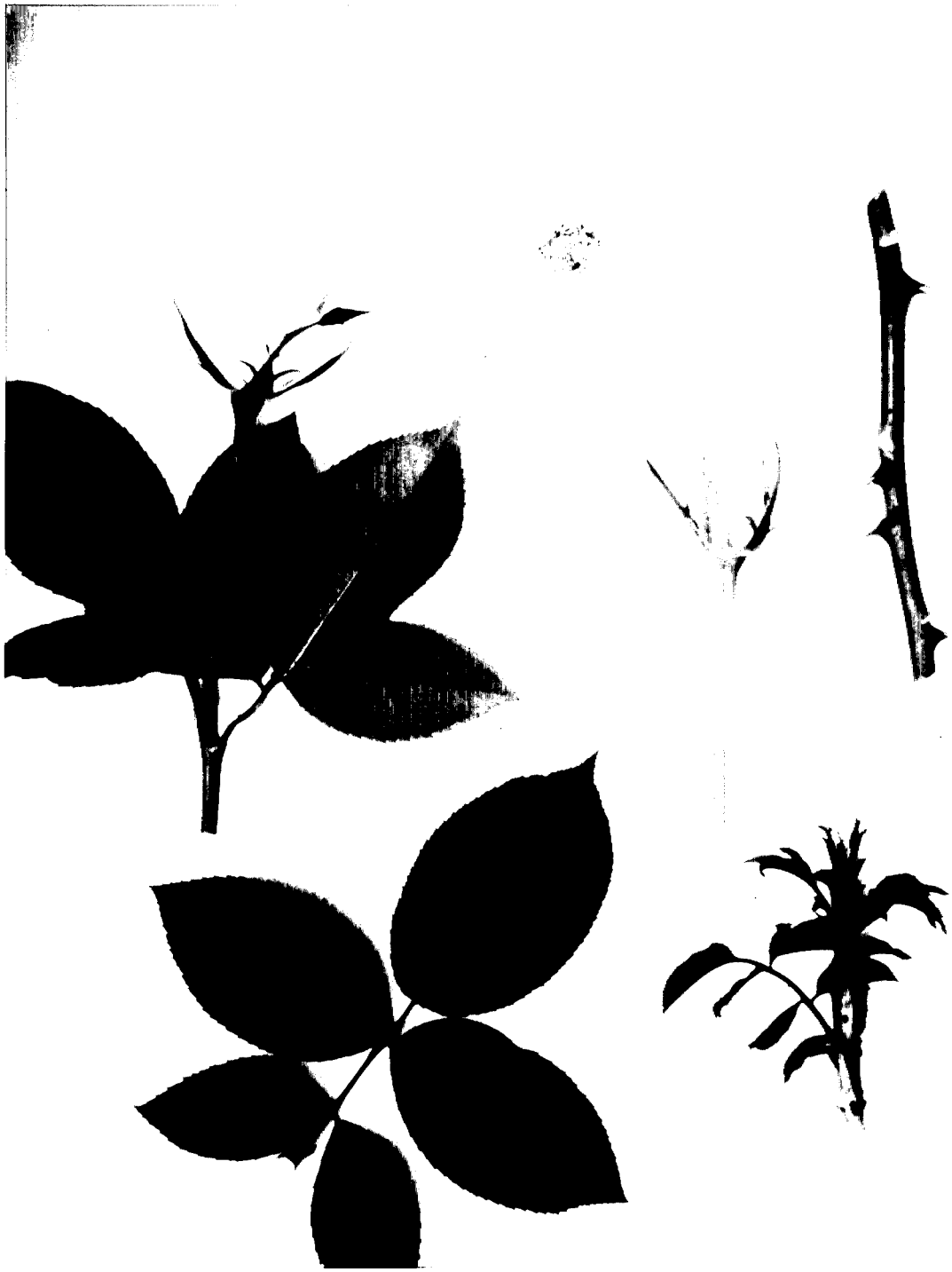

Warriner

[11] Patent Number: Plant 5,743

[45] Date of Patent: May 13, 1986

[54] ROSE PLANT JACICE

[75] Inventor: William A. Warriner, Tustin, Calif.

[73] Assignee: Jackson & Perkins Company, Medford, Oreg.

[21] Appl. No.: 656,920

[22] Filed: Oct. 1, 1984

[51] Int. Cl.[4] ..... A01H 5/00

[52] U.S. Cl. ..... Plt./14

[58] Field of Search ..... Plt./14

*Primary Examiner*—James R. Feyrer

*Attorney, Agent, or Firm*—Manford R. Haxton

[57] ABSTRACT

A hybrid tea rose variety having nearly pure white buds and open flowers, long stems, few thorns and large disease resistant foliage.

1 Drawing Figure

This present invention relates to a new and distinct variety of rose plant of the hybrid tea class which was originated by crossing the variety Coquette, U.S. Plant Pat. No. 4,019, with an unnamed variety.

The primary objective of this breeding was to produce a new rose variety suitable for use to produce cut blooms in greenhouses, of a white color, pointed bud form, attractive foliage. This objective was substantially achieved along with other desirable improvements as evidenced by the following unique combination of characteristics which are outstanding in the new variety and which distinguish it from its parents as well as from all other varieties of which I am aware:

1. Nearly pure white, pointed buds;
2. Long, rigid stems with few thorns;
3. Large, deep green, mildew resistant foliage;
4. Very slight fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:
- *Seed parent.*—Coquette, U.S. Plant Pat. No. 4,019.
- *Pollen parent.*—Unnamed variety.

Classification:
- *Botanical.*—Rosa hybrid.
- *Commercial.*—Hybrid tea.

FLOWER

Observations made from specimens grown in a greenhouse at Irvine, Calif., in July.

Blooming habit: Continuous.

Bud:
- *Size.*—1¼" when petals start to unfurl.
- *Form.*—Long, narrow.
- *Color.*—When sepals first divide, Near White; when half blown, upper side of petals, Near White; lower side of petals, Near White.

- *Sepals.*—Color: Green 138B. Three appendaged sepals lightly appendaged and glandular. Two appendaged sepals hairy edged and glandular.
- *Receptacle.*—Color: Green 138B. Shape: Funnel. Size: Small. Surface: Slightly hairy.
- *Peduncle.*—Length: Medium. Surface: Lightly prickly. Color: Light green. Strength: Stiff, erect.

Open bloom:
- *Size.*—Medium. Average open size 4".
- *Borne.*—Singly.
- *Stems.*—Long, strong.
- *Form.*—When first open, high center. Permanence: All petals curl.
- *Petalage.*—Number of petals under normal conditions: 32.
- *Color.*—Center of flower: Upper side of petals, Near White; reverse side of petals, Near White. Base of petals, Tint of Yellow 6D. Major color: White.
- *Fragrance.*—Slight.

Petals:
- *Texture.*—Thick.
- *Shape.*—Round.
- *Form.*—Edges slightly quilled.
- *Arrangement.*—Imbricated. Petaloids in center, few.
- *Persistence.*—Drop off cleanly.
- *Lastingness.*—On the plant, long. As cut flower, long.

Reproductive parts:
- *Anthers.*—Medium. Color: Yellow. Arrangement: Regular around styles.
- *Filaments.*—Color: Near Yellow Green 145D.
- *Pollen.*—Lemon Yellow.
- *Styles.*—Color: Red distal portion, white proximal portion.
- *Stigmas.*—Color: White.

PLANT

Form: Bush.

Growth: Very vigorous, upright.

Foliage: Number of leaflets on normal mid-stem leaves: 5 or 7.
- *Size.*—Very large.
- *Quantity.*—Normal.
- *Color.*—New foliage: Near Greyed Purple 183B. Old foliage: Green 139A.

Leaflets:
- *Shape.*—Pointed, elliptic.

*Texture.*—Leathery.

*Edge.*—Serrated.

*Serration.*—Single, small.

*Petiole.*—Rachis: Color: Green. Upper edges with rows of stipitate glands. Underside: With prickles.

*Stipules.*—Medium, bearded.

*Disease resistance.*—Resistant to mildew, under normal growing conditions at Irvine, Calif.

Wood:

*New wood.*—Color: Light green. Bark: Smooth.

*Old wood.*—Color: Green. Bark: Smooth.

Prickles:

*Quantity.*—On main canes from base: Few. On laterals from main canes: Few.

*Form.*—Long, straight.

*Color when young.*—Brown.

I claim:

1. A new and distinct variety of rose plant of the hybrid tea class, substantially as herein shown and described, characterized particularly as to novelty by the unique combination of its nearly pure white buds and open flowers, long stems, few thorns and large disease resistant foliage.

* * * * *